(12) United States Patent
Park et al.

(10) Patent No.: US 8,293,556 B2
(45) Date of Patent: Oct. 23, 2012

(54) FABRICATING METHOD FOR MICRO GAS SENSOR AND THE SAME

(75) Inventors: Kwang Bum Park, Gyungkido Yonginsi (KR); Seong Dong Kim, Gyungkido Yonginsi (KR); Joon Shik Park, Seoul (KR); Min Ho Lee, Seoul (KR)

(73) Assignee: Korea Electronics Technology Institute, Seongnam, Gyeonggi Province (KR)

( * ) Notice: Subject to any disclaimer, the term of this patent is extended or adjusted under 35 U.S.C. 154(b) by 152 days.

(21) Appl. No.: 12/810,850

(22) PCT Filed: Dec. 26, 2008

(86) PCT No.: PCT/KR2008/007701
§ 371 (c)(1),
(2), (4) Date: Sep. 2, 2010

(87) PCT Pub. No.: WO2009/084871
PCT Pub. Date: Jul. 9, 2009

(65) Prior Publication Data
US 2010/0314700 A1 Dec. 16, 2010

(30) Foreign Application Priority Data
Dec. 26, 2008 (KR) .................. 10-2007-0141055

(51) Int. Cl.
*H01L 21/00* (2006.01)
*G01N 9/00* (2006.01)

(52) U.S. Cl. .................. 438/49; 257/414; 257/E21.004; 73/31.06

(58) Field of Classification Search .................. 257/414, 257/E21.004; 438/49; 73/31.06
See application file for complete search history.

(56) References Cited

U.S. PATENT DOCUMENTS

| 6,326,228 B1 * | 12/2001 | Hughes et al. .................. 438/49 |
| 6,997,040 B1 * | 2/2006 | Lee et al. ..................... 73/31.05 |
| 2002/0142478 A1 * | 10/2002 | Wado et al. .................... 436/151 |
| 2003/0037590 A1 * | 2/2003 | Stark .............................. 73/1.03 |

(Continued)

FOREIGN PATENT DOCUMENTS

| JP | 09318569 | 12/1997 |
| KR | 1019950021549 | 2/1997 |
| KR | 1020027002442 | 7/2002 |

(Continued)

*Primary Examiner* — Steven J Fulk
(74) *Attorney, Agent, or Firm* — Lowe Hauptman Ham & Berner, LLP (57) ABSTRACT

There are provided a micro gas sensor and a method for fabricating the same that comprises a micro heater formed inside a polysilicon membrane by doping impurities into a specific region of the polysilicon membrane positioned under a gas sensing substance, thereby improving thermal structural stability and making it easy to form the gas sensing substance. The micro gas sensor comprises: a micro heater formed by doping impurities into polysilicon vapor-deposited on a substrate on which a first insulating layer is formed; a polysilicon membrane for decreasing a heat loss of the micro heater; a power electrode for supplying power and a temperature measurement electrode for measuring a temperature, positioned at both ends of the micro heater; a second insulating layer formed on the micro heater; a sensing substance formed on the second insulating layer, for sensing a gas; and a sensing electrode for measuring a change in properties of the sensing substance. The method for fabricating a micro gas sensor comprises steps of: forming polysilicon on a substrate on which a first insulating layer is formed; forming a micro heater by doping impurities into the polysilicon; forming electrodes at both ends of the micro heater; forming a second insulating layer on the micro heater; forming a sensing substance on the second insulating layer; and forming a sensing electrode on the sensing substance.

14 Claims, 6 Drawing Sheets

U.S. PATENT DOCUMENTS

| | | | |
|---|---|---|---|
| 2004/0021184 A1* | 2/2004 | Benzel et al. | 257/414 |
| 2004/0147057 A1* | 7/2004 | Benzel et al. | 438/54 |
| 2005/0186696 A1* | 8/2005 | Yamada et al. | 438/48 |
| 2006/0154401 A1* | 7/2006 | Gardner et al. | 438/53 |
| 2008/0134753 A1* | 6/2008 | Jun et al. | 73/23.2 |

FOREIGN PATENT DOCUMENTS

| | | |
|---|---|---|
| KR | 1020030085552 | 6/2005 |
| KR | 1020060049677 | 11/2007 |
| WO | WO 2007026177 A1 * | 3/2007 |

* cited by examiner

FABRICATING METHOD FOR MICRO GAS SENSOR AND THE SAME

This application is a National Stage of PCT/KR 2008/007701 filed on Dec. 26, 2008, which claims priority of Korean Patent Application No. 10-2007-0141055 filed Dec. 28, 2007.

TECHNICAL FIELD

The present invention relates to a gas sensor and, more particularly, to a micro gas sensor and a method for fabricating the same that comprises a micro heater formed inside a polysilicon membrane by implanting ions or doping impurities into a specific region of the polysilicon membrane positioned under a gas sensing substance, whereby thermal stability is high and a gas sensing substance is easily and efficiently formed.

BACKGROUND ART

Figure 1:
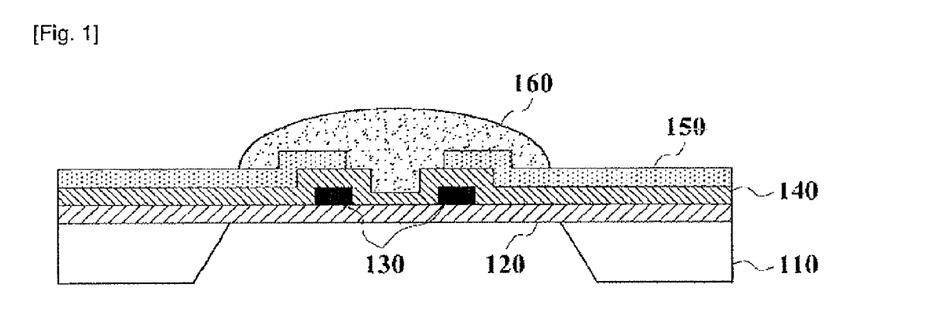
FIG. 1 is a circuit diagram illustrating a conventional gas sensor.

FIG. 1 is a sectional view of a conventional micro gas sensor.

The conventional micro gas sensor comprises: a substrate 110, a membrane 120, a micro heater 130, an insulating layer 140, a sensing electrode 150 and a gas sensing substance 160. After the membrane 120 and the micro heater 130 are sequentially formed on the substrate 110, the insulating layer 140 is formed thereon. The sensing electrode 150 and the gas sensing substance 160 are formed on the insulating layer 140. The micro heater 130 formed on the membrane 120 is formed with an irregular thickness. Consequently, the insulating layer 140 formed in a subsequent process is irregular in thickness by the irregular thickness of the micro heater 130.

When the micro gas sensor having the aforementioned irregular structure is operated at a high temperature for a long time, since materials around the micro heater 130 have different thermal expansion properties, internal stress is generated at the boundary position between the materials and the micro heater 130 by heat. As a result, the insulating layer 140 is broken, causing problems in electrifying the sensing electrode and the micro heater and making it difficult to maintain durability for a long time.

Further, when an array sensor of high density is manufactured by using a nano wire composed of the material, such as SnO2, ZnO or the like, or a nano particle sensing substance, the sensing substance is formed, using a contact printing method. Then, the conventional gas sensor has the problem in that it is difficult to form the sensing substance by the contact printing method due to the irregular surface around the micro heater.

DISCLOSURE OF INVENTION

Technical Problem

Therefore, the present invention has been made to solve the above problems, and it is an aspect of the present invention to provide a micro gas sensor and a method for fabricating the same in that a micro heater is formed inside a polysilicon membrane by doping impurities in a predetermined concentration to the polysilicon membrane, without forming any irregular structure, whereby durability is outstanding even for long-time operation, a high-density array sensing substance is easily formed and therefore gas sensing sensitivity is excellent.

Technical Solution

In accordance with the present invention, the above and other aspects can be accomplished by a micro gas sensor comprising: a micro heater formed by doping impurities into polysilicon deposited on a substrate on which a first insulating layer is formed; a polysilicon membrane for decreasing a heat loss of the micro heater; a power electrode for supplying power and a temperature measurement electrode for measuring a temperature, positioned at both ends of the micro heater; a second insulating layer formed on the micro heater; a sensing substance formed on the second insulating layer, for sensing a gas; and a sensing electrode for measuring a change in properties of the sensing substance.

In accordance with the present invention, the above and other aspects can be also accomplished by a method for fabricating a micro gas sensor, comprising steps of: forming polysilicon on a substrate on which a first insulating layer is formed; forming a micro heater by doping impurities into the polysilicon; forming electrodes at both ends of the micro heater; forming a second insulating layer on the micro heater; forming a sensing substance on the second insulating layer; and forming a sensing electrode on the sensing substance.

Advantageous Effects

The micro gas sensor and the method for fabricating the same according to the present invention has the significant and favorable effects in that durability is outstanding even for long-time operation, gas sensing sensitivity through a high-dense array sensor is excellent, and many kinds of gases are sensed.

BRIEF DESCRIPTION OF DRAWINGS

These and other aspects and advantages of the present invention will become apparent and more readily appreciated from the following description of the embodiments, taken in conjunction with the accompanying drawings, in which.

BEST MODE FOR CARRYING OUT THE INVENTION

The present invention will now be described more fully hereinafter with reference to the accompanying drawings, in which preferred embodiments of the invention are shown.

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

The present invention may be embodied in different forms and should not be construed as limited to the embodiments set forth herein. Rather, these embodiments are provided as teaching examples of the invention. Therefore, it will be understood that the scope of the invention is intended to include various modifications and alternative arrangements within the capabilities of persons skilled in the art using presently known or future technologies and equivalents.

FIGS. 2 through 10 are process flow charts illustrating a micro gas sensor according to the present invention.

Figure 2:
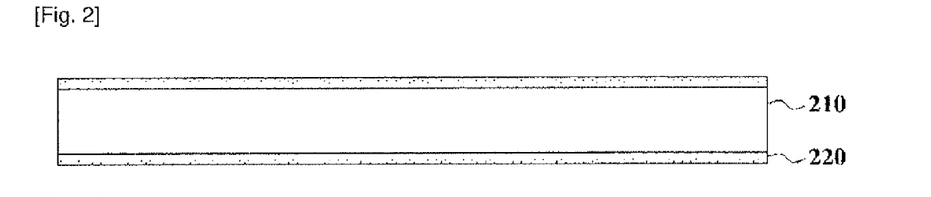
FIGS. 2 through 10 are process flow charts illustrating a micro gas sensor according to the present invention.
Figure 3:
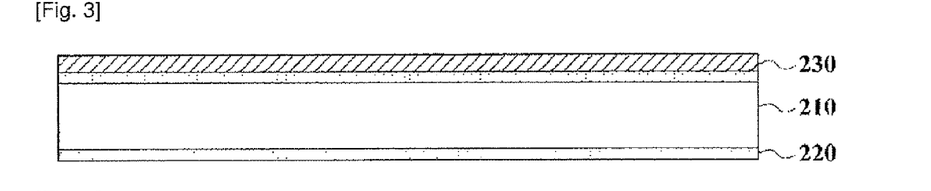

As illustrated in FIG. 2, a first insulating layer 220 including a silicon oxide layer of a predetermined thickness is formed on both sides of a silicon substrate 210 by thermal oxidation or low-pressure chemical vapor deposition (LPCVD). As illustrated in FIG. 3, a layer of polysilicon 230 is deposited on the first insulating layer 220 to a thickness of 0.4~2 μm by the LPCVD process.

Polysilicon 230 according to the present invention is used in fabricating a membrane and a micro heater for thermal isolation.

Figure 4:
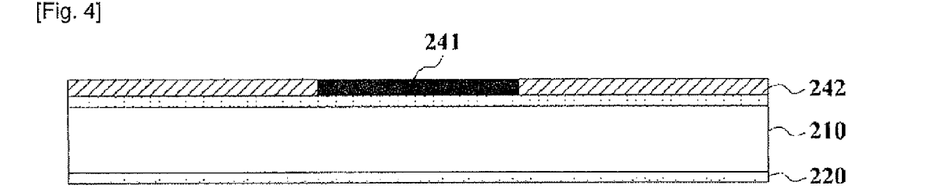

As illustrated in FIG. 4, impurities (dopant), such as boron, phosphorus, phosphorus chloride (POC13), or the like, are doped into a partial region of the deposited polysilicon 230 by thermal expansion, ion implantation and the like, to give conductivity to a predetermined region inside the polysilicon 230 which is an insulator. Preferably, a depth to which the impurities are doped into the polysilicon 230 may be equal to or less than the thickness of the polysilicon 230.

The polysilicon 230 where the impurities are not doped functions as a membrane which is an insulator.

The depth to which the impurities are doped into the polysilicon 230 is equal to or less than the thickness of the polysilicon 230. The impurities are doped to a depth of a partial or total thickness of the polysilicon 230, to form a micro heater 241 of conductivity.

The polysilicon 230, which has the conductivity as the impurities are doped, functions as the micro heater 241. In a region of the micro heater 241, the Joule heat is generated by power applied from the outside, operating as a heater. Since a part of the micro heater 241, which is the region doped with the impurities inside the polysilicon 230, and the membrane 242, which is the polysilicon 230 where the impurities are not doped, are basically made of a polysilicon material, a difference in thermal expansion therebetween is small. Therefore, durability of the membrane 242 according to driving of the micro heater 241 is improved.

In accordance with an embodiment of the present invention, the micro heater may be formed in a zigzag pattern.

When the micro heater 241 is formed by doping the impurities into the polysilicon 230, since the micro gas sensor according to the present invention has no irregular structure unlike the conventional art, the flatness of the membrane 242 is maintained. Therefore, it is possible to fabricate a high-density gas sensor array using a sensing substance of high-sensitivity by a contact printing process, a nano imprinting process, a drop dispensing process or the like.

Figure 5:
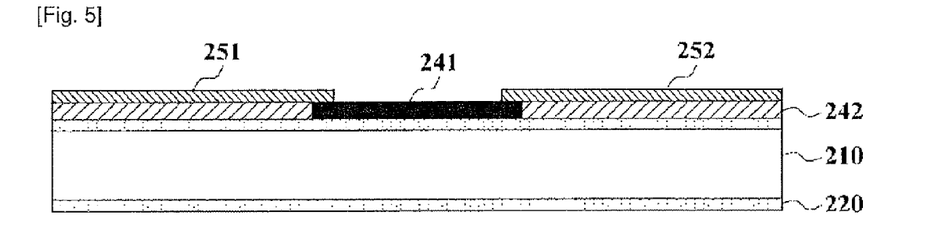

As illustrated in FIG. 5, a plurality of power electrodes 251 for applying power to the micro heater 241 and a plurality of temperature measurement electrodes 252 for measuring a temperature of the micro heater 241 are formed. The power electrode 251 and the temperature measurement electrode 252 are formed, using the same metal. The power electrode 251 and the temperature measurement electrode 252 are formed by a photo etching process after aurum (Au) or platinum (Pt) is vapor-deposited to contact with both ends of the micro heater 241.

A constant current A is applied through the power electrode 251, to operate the micro heater 241. At the same time, a voltage V applied to both ends of the micro heater 241 is measured through the temperature measurement electrode 252, and a resistance value of the micro heater 241 is calculated based on a relational expression, V=IR. A temperature of the micro heater 241 can be measured by using a coefficient of temperature resistance of the micro heater 241. An electric circuit is configured by feeding back the measured temperature of the micro heater 241, so that the temperature of the micro heater 241 can be consistently maintained.

Figure 6:
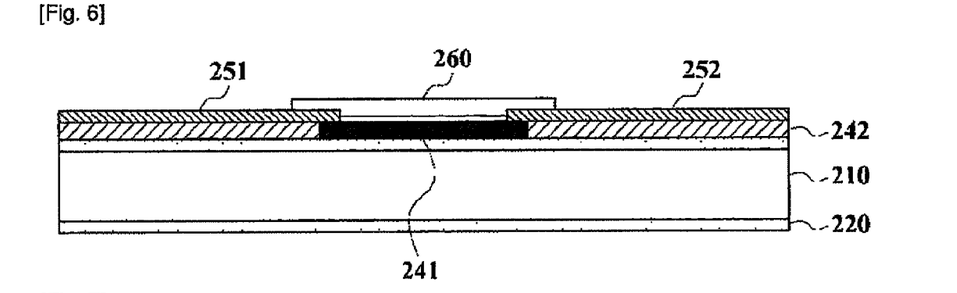

As illustrated in FIG. 6, a second insulating layer 260 is formed in a predetermined region on the micro heater 241. The second insulating layer 260 includes a silicon oxide layer or nitride layer for the electrical insulation among the micro heater 241, the power electrode 251, the temperature measurement electrode 252 and a sensing electrode 280 (shown in FIG. 8). Since the second insulating layer 260 is formed on the micro heater 241 formed by doping the impurities, the irregular structure of the conventional art is not formed and therefore a decrease in durability which is caused by thermal stress is minimized.

Figure 7:
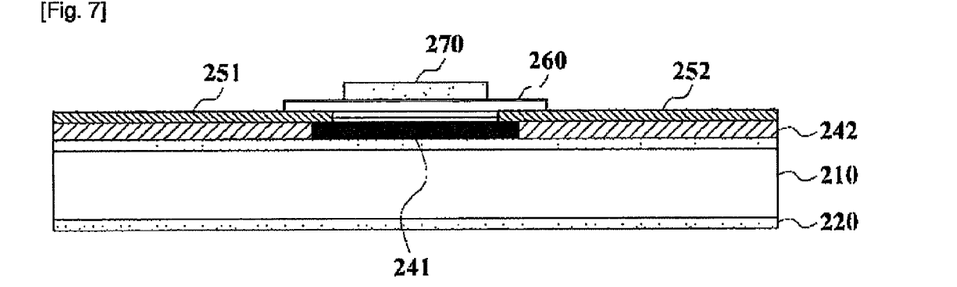

When the second insulating layer 260 is formed, a sensing substance 270 for sensing a gas is formed as illustrated in FIG. 7. A process of forming the sensing substance 270 is performed, using a drop process, a screen printing process, a photolithography process, a contact printing process, a nano imprint process, or the like. Specifically, since nano sensing substances of high-sensitivity are formed by using the contact printing process, nano imprint process or drop dispensing process, the surface of the sensing substances is formed with excellent flatness, making it possible to fabricate the high-density sensing sensor array.

Figure 8:
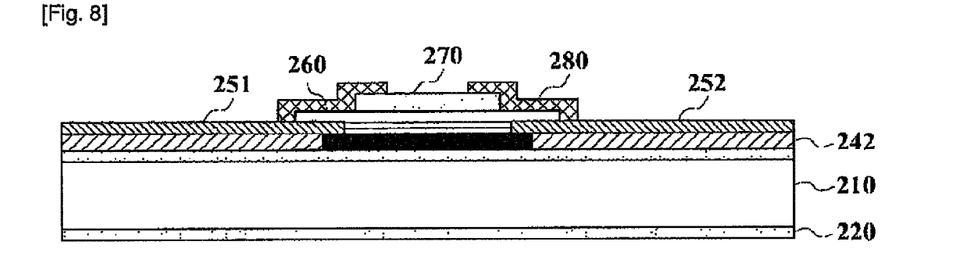

When the sensing substance 270 is formed, a sensing electrode 280 is formed as illustrated in FIG. 8. The sensing electrode 280 measures a change in properties of the sensing substance 270 as a result of sensing a gas. Then, the sensing electrode 280 uses the material, such as aurum (Au) or platinum (Pt), which has small reactivity with other materials.

In accordance with another embodiment of the present invention, the process of forming the sensing electrode 280 (in FIG. 8) may be performed prior to the process of forming the sensing substance 270 (in FIG. 7).

Figure 9:
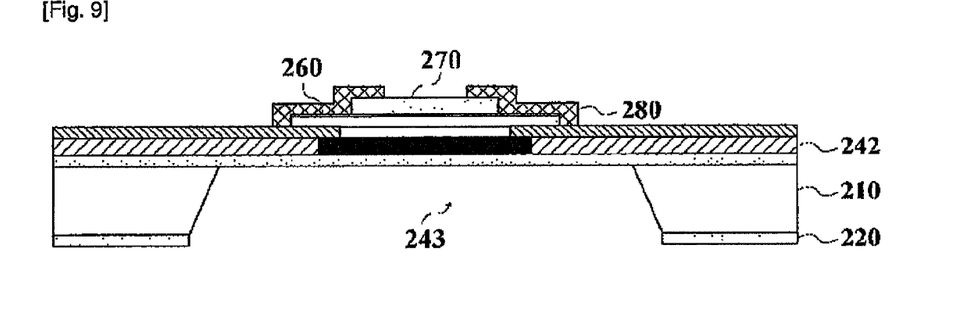

When the sensing electrode 280 is formed, the first insulating layer 220 formed on the back side of the silicon substrate 210 is etched by using a buffed oxide etchant (BOE) or steam HF as illustrated in FIG. 9, to minimize the transfer of heat generated in the micro heater 241 to its around structure. The exposed substrate 210 is etched, using KOH, TMAH or Deep RIE, to form a cavity 243 to expose the first insulating layer 220 formed on the substrate 210.

Figure 10:
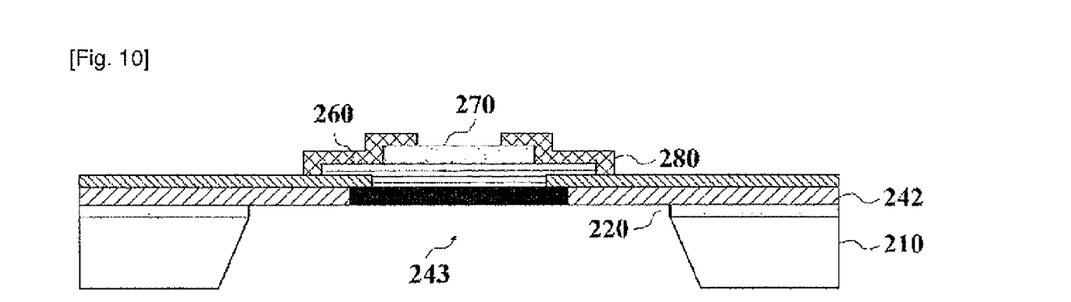

As illustrated in FIG. 10, the first insulating layer 220 is again etched by the BOE or steam HF until the polysilicon is exposed. Then, the exposed polysilicon functions as the membrane 242.

FIGS. 11 through 15 are plan views illustrating a micro gas sensor according to another embodiment of the present invention, which is capable of sensing various kinds of gases.

Figure 11:
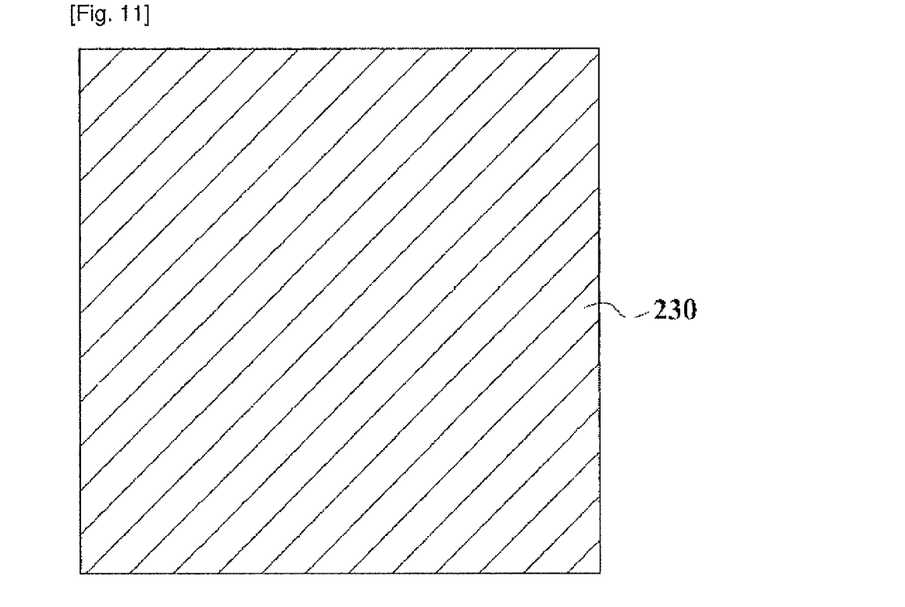
FIGS. 11 through 15 are process flow charts illustrating a micro gas sensor according to an embodiment of the present invention.
Figure 12:
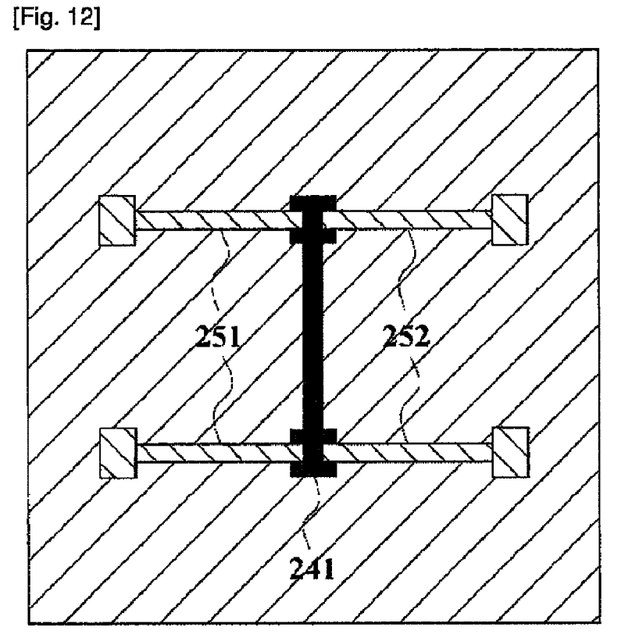
Figure 13:
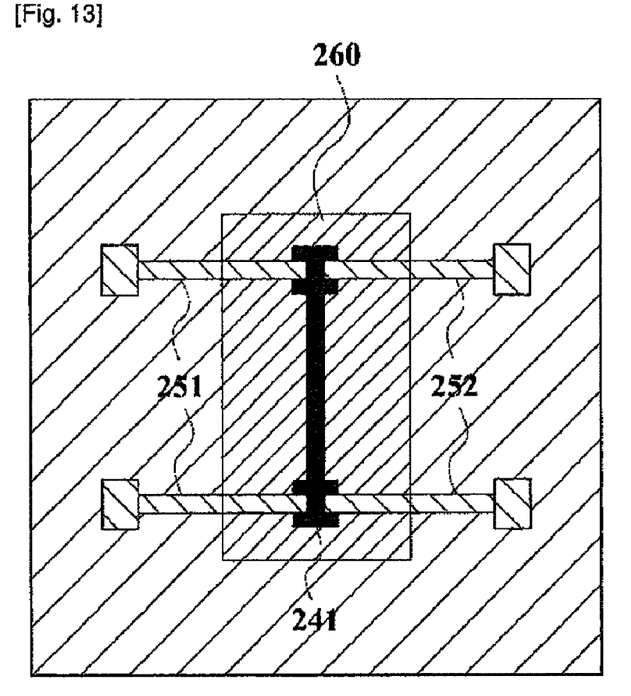
Figure 14:
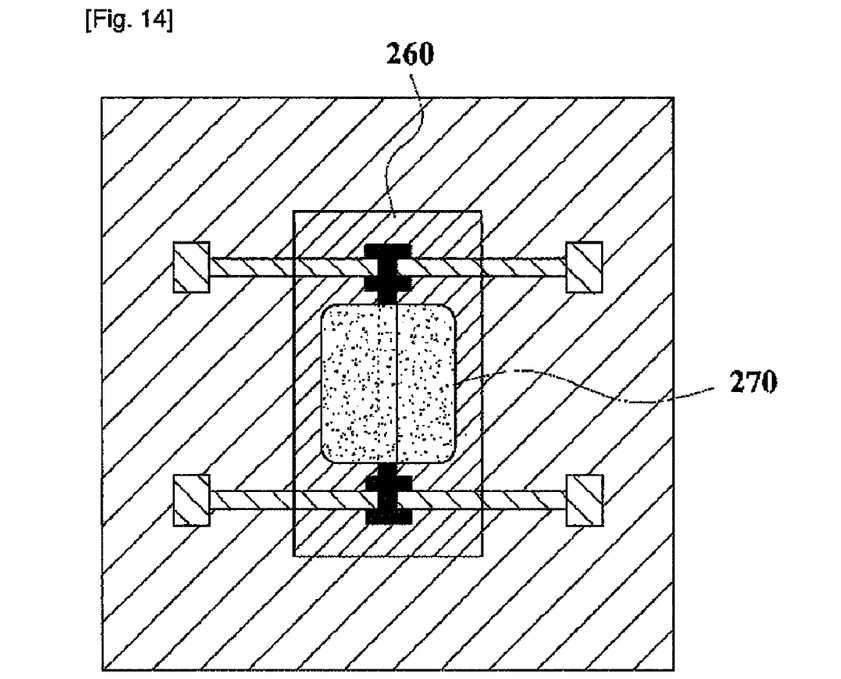
Figure 15:
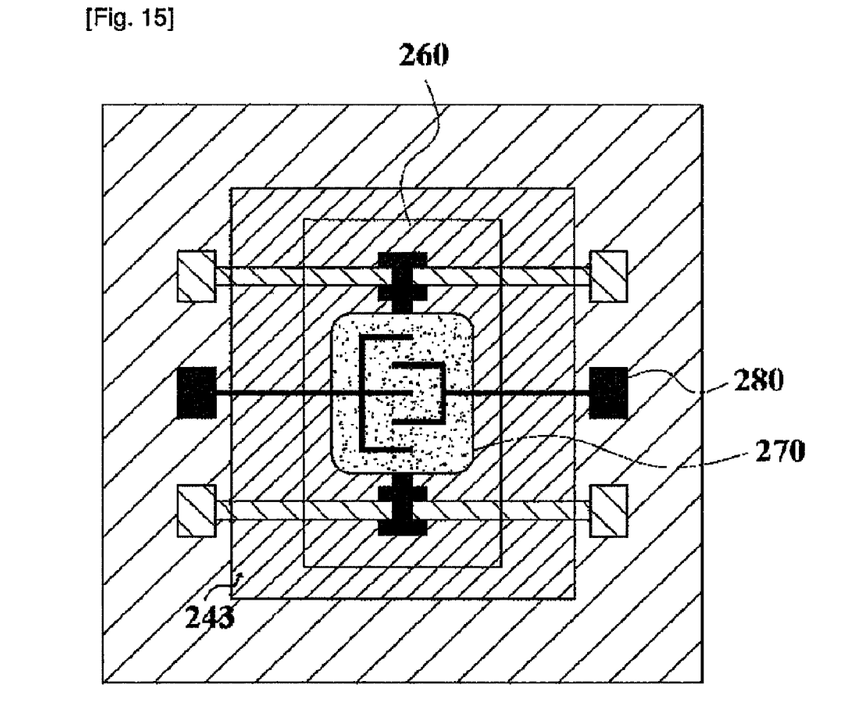

In FIG. 11, polysilicon 230 is formed on a substrate on which a first insulating layer is formed. In FIG. 12, a micro heater 241 is formed by doping impurities into a pre-determined region of the polysilicon 230, and a power electrode 251 and a temperature measurement electrode 252 are formed. In FIG. 13, a second insulating layer 260 covering the micro heater 241 is formed, and in FIG. 14, a sensing substance 270 is formed. In FIG. 15, a sensing electrode 280 is formed across the sensing substance 270 and the back side of the substrate is etched to form a cavity 243, thereby completing a micro gas sensor comprising a polysilicon membrane 242 (refer to FIG. 10) including the micro heater.

Preferably, the sensing electrode 280 formed on the micro heater 241 may be formed by using an IDT (inter-digitized) structure, to improve an area of the electrode to improve the sensitivity of the senor.

Figure 16:
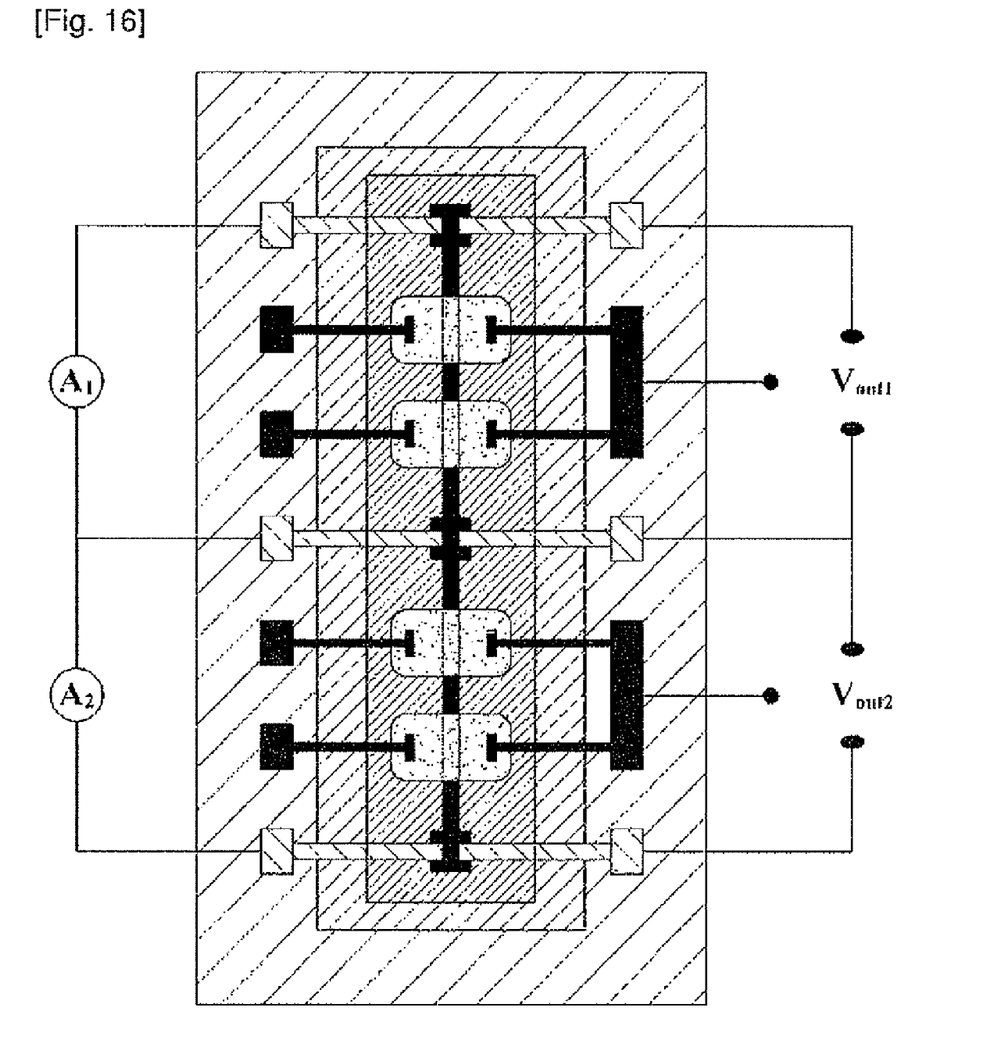
FIG. 16 is a plan view illustrating a micro gas sensor according to another embodiment of the present invention.

FIG. 16 illustrates a micro gas sensor according to another embodiment of the present invention.

Since a temperature at which a sensing substance operates is different depending on a kind of a gas, a plurality of power electrodes is formed to apply a plurality of constant currents A1 and A2, to differently control the temperature of operating the micro heater. Furthermore, a plurality of temperature measurement electrodes is formed to measure the temperature by measuring voltages Vout1 and Vout2 applied to both ends of the micro heater operated at different temperatures.

Furthermore, each micro heater includes a plurality of gas sensors, to increase the reliability of gas-sensing. To decrease the number of electrode pads in the plurality of gas sensors, a plurality of electrodes at one side is unified as a common electrode. An electric circuit may be formed to sequentially measure a sensor array, by using a multiplexer (MUX) through an individual sensing electrode at the other side.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A micro gas sensor comprising:
    a micro heater formed by doping impurities into polysilicon vapor-deposited on a substrate on which a first insulating layer is formed, wherein the micro heater has a planar surface;
    a polysilicon membrane for decreasing a heat loss of the micro heater, wherein a region of the polysilicon non-doped with the impurities is defined as the membrane, and wherein the micro heater and the membrane are formed at the same level of height;
    a power electrode for supplying power and a temperature measurement electrode for measuring a temperature, positioned at both ends of the micro heater;
    a second insulating layer formed on the micro heater and between the power electrode and the temperature measurement electrode, wherein the second insulating layer has a planar surface in consistent with the planar surface of the micro heater;
    a sensing substance formed on the second insulating layer, for sensing a gas; and
    a sensing electrode for measuring a change in properties of the sensing substance.

2. The micro gas sensor according to claim 1, wherein a depth to which the impurities are doped into the polysilicon is equal to or less than a thickness of the polysilicon.

3. The micro gas sensor according to claim 1, further comprising:
    a cavity formed by etching the first insulating layer and the substrate under a region where the micro heater is formed.

4. The micro gas sensor according to claim 1, wherein a plurality of the micro heaters is formed.

5. The micro gas sensor according to claim 1, wherein a plurality of the power electrodes and a plurality of the temperature measurement electrodes are formed.

6. The micro gas sensor according to claim 1, wherein the sensing electrode is formed on or at the side of a structure of the micro heater.

7. The micro gas sensor according to claim 1, wherein the micro heater or the sensing electrode is an IDT (inter-digitized) structure.

8. The micro gas sensor according to claim 1, wherein the impurities are any one of POC13, boron and phosphorus.

9. The micro gas sensor according to claim 1, wherein a material of the power electrode is aurum or platinum.

10. The micro gas sensor according to claim 1, wherein the power electrode is connected to a constant current power source.

11. A method for fabricating a micro gas sensor comprising steps of:
    forming polysilicon on a substrate on which a first insulating layer is formed;
    forming a micro heater by doping impurities into the polysilicon, wherein a partial region of the polysilicon doped with the impurities is defined as the micro heater and the remaining region of the polysilicon non-doped with the impurities is defined as a membrane for decreasing heat loss of the micro heater, wherein the micro heater and the membrane are formed at the same level of height, and wherein the micro heater has a planar surface;
    forming electrodes at both ends of the micro heater and on the membrane;
    forming a second insulating layer on the micro heater and between the electrodes, wherein the second insulating layer has a planar surface in consistent with the planar surface of the micro heater;
    forming a sensing substance on the second insulating layer; and
    forming a sensing electrode on the sensing substance.

12. The method according to claim 11, further comprising a step of:
    forming a cavity by etching the first insulating layer and the substrate formed under a region including the micro heater.

13. The method according to claim 12, wherein the etching uses KOH, TMAH or Deep RIE.

14. The method according to claim 11, wherein the sensing substance is formed, using any one of contact printing, nano imprinting and drop dispensing.

* * * * *